United States Patent [19]

Isshiki et al.

[11] 4,234,733

[45] Nov. 18, 1980

[54] PROCESS FOR PRODUCING ALIPHATIC CARBOXYLIC ACIDS AND ALIPHATIC CARBOXYLIC ACID ESTERS OF PHENOLS

[75] Inventors: Tomiya Isshiki, Tokyo; Yasuhiko Kijima; Yuh Miyauchi, both of Matsudo, all of Japan

[73] Assignee: Mitsubishi Gas Chemical Company, Inc., Tokyo, Japan

[21] Appl. No.: 954,171

[22] Filed: Oct. 24, 1978

[30] Foreign Application Priority Data

Oct. 28, 1977 [JP] Japan ................. 52/129438

[51] Int. Cl.³ ............. C07C 51/09; C07C 51/12; C07C 27/00; C07D 215/32
[52] U.S. Cl. .................. 546/174; 260/351; 260/376; 260/465 D; 560/130; 560/139; 562/517; 562/519; 560/141; 560/142; 560/144; 560/146
[58] Field of Search ............. 562/517, 519; 560/130, 560/139, 141, 142, 144, 146; 260/351, 376, 465 D; 546/174

[56] References Cited

U.S. PATENT DOCUMENTS

| 3,769,324 | 10/1973 | Paulik et al. | 562/519 |
|---|---|---|---|
| 3,769,326 | 10/1973 | Paulik et al. | 562/519 |
| 3,769,329 | 10/1973 | Paulik et al. | 562/519 |
| 3,813,428 | 5/1974 | Paulik et al. | 562/519 |

Primary Examiner—Jane S. Myers
Attorney, Agent, or Firm—Wenderoth, Lind & Ponack

[57] ABSTRACT

A process for producing an aliphatic carboxylic acid and an aliphatic carboxylic acid esters ofa phenol which comprises reacting a phenol of the general formula

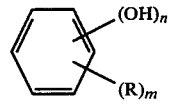

wherein n is an integer of 1 to 6, m is an integer of 0 to 5, the sum of n and m is 6, and R represents hydrogen, alkyl, aryl, alkenyl, carbinol, acyl, acyloxy, formyl, carboxy, halogen, sulfo, nitro, nitroso, amino, amido, or cyano, and two or more R groups may be the same or different, and the substituents R may be bonded to each other to form a penta- or hexa-carboxylic or heterocyclic ring, and an aliphatic carboxylic acid ester or an aliphatic ether with carbon monoxide, and separating and recovering the aliphatic carboxylic acid from the reaction mixture.

4 Claims, No Drawings

PROCESS FOR PRODUCING ALIPHATIC CARBOXYLIC ACIDS AND ALIPHATIC CARBOXYLIC ACID ESTERS OF PHENOLS

This invention relates to a process for producing carboxylic acids and carboxylic acid esters of phenols by reacting phenols and aliphatic carboxylic acid esters or aliphatic ethers with carbon monoxide.

A process for producing carboxylic acids by the carbonylation reaction of alcohols is typically known in a process for producing acetic acid from methanol and carbon monoxide. For example, U.S. Pat. Nos. 2,729,651 and 2,727,902 and German Pat. Nos. 921,938, 933,148, and 947,469 describe processes which comprise reacting an alcohol, ether or ester with carbon monoxide in the presence of, as a catalyst, a transition metal such as iron, cobalt or nickel and a compound of a halogen such as iodine or bromine (the Reppe process).

All of these processes require severe conditions involving high temperatures and pressures, and can give only unsatisfactory yields. In recent years, a process which comprises using a catalyst composed of a complex of a platinum-group metal typified by rhodium was developed in an attempt to remove these defects (Japanese Patent Publications Nos. 3331/72 to 3337/72 which correspond to U.S. Applications Ser. Nos. 701637 to 701639, 628577, 628578, 628581 and 628591). According to this process, the carbonylation reaction can be performed under milder conditions than in the Reppe process using a platinum-group metal complex. The superiority of this process is also shown by the reduced amounts of by-products and therefore the good yields of the desired product. However, various side-reactions occur in this process to form water, hydrogen halide, etc. Furthermore, when an ester or ether is used as a starting material, the presence of water in the reaction system is necessary. The presence of these substances in the reaction system causes the formation of a corrosive atmosphere, and consideration must be given to the quality of the reactor material. Moreover, the resulting carboxylic acid must be separated from water.

It is an object of this invention therefore to provide a process for producing aliphatic carboxylic acids and aliphatic carboxylic acid esters of phenols which removes the aforesaid defects of the prior art processes and does not form water, hydrogen halide, etc. as by-products.

The present inventors undertook extensive work in order to achieve the above object, and found that when a phenol and an aliphatic carboxylic acid ester or an aliphatic ether are reacted with carbon monoxide, the desired aliphatic carboxylic acid can be easily formed in high yields together with the carboxylic acid ester of the phenol without forming water, hydrogen halide, etc. and requiring the presence of water by the following reaction formula.

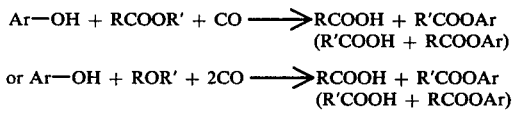

(Ar represents a substituted or unsubstituted aryl group, and R and R' represent an aliphatic group.) It has also been found that the carboxylic acid ester of the phenol thus obtained can be reused by reacting it with an aliphatic alcohol to convert it into an aliphatic carboxylic acid ester and a phenol.

According to this invention, there is provided a process for producing an aliphatic carboxylic acid and an aliphatic carboxylic acid ester of a phenol which comprises reacting a phenol having 6 to 30 carbon atoms of the general formula

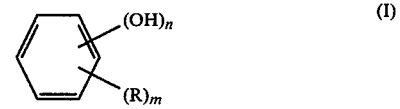

wherein n is an integer of 1 to 6, m is an integer of 0 to 5, the sum of n and m is 6, and R represents hydrogen, alkyl, aryl, alkenyl, hydroxymethyl, acyl, acyloxy, formyl, carboxy, halogen, sulfo, nitro, nitroso, amino, acid amide, or cyano, and two or more R groups are the same or different, and the substituents R may be bonded to each other to form a penta or hexa carbocyclic or heterocyclic ring, and an aliphatic carboxylic ester or an aliphatic ether with carbon monoxide, and separating and recovering the aliphatic carboxylic acid from the reaction product.

Examples of the phenol of formula (I) include phenol, cresol, xylenol, trimethylphenol, tetramethylphenol, pentamethylphenol, ethylphenol, propylphenol, thymol, carvacrol (2-methyl-5-isopropylphenol), butylphenol, amylphenol, octylphenol, methyldibutylphenol, diethylphenol, catechol, resorcinol, hydroquinone, dihydroxytoluene, hexylresorcinol, pyrogallol, phloroglucinol, chlorophenol, bromophenol, nitrophenol, nitrosophenol, aminophenol, N,N-dimethylaminophenol, N-methyl-N-acetylphenol, acetyloxyphenol, formylphenol, cyanophenol, phenolsulfonic acid, (hydroxymethyl)phenol, naphthol, dihydroxynaphthalene, dihydronaphthol, tetrahydronaphthol, phenylphenol, hydroxyquinolin, anthrahydroquinone, methylanthrahydroquinone, ethylanthrahydroquinone, amylanthrahydroquinone, and 1,2-dihydroxyanthraquinone (alizarin).

Esters formed between aliphatic carboxylic acids having 1 to 5 carbon atoms and alcohols having 1 to 4 carbon atoms are suitable aliphatic carboxylic acid esters used in this invention. Examples include methyl formate, propyl formate, methyl acetate, ethyl acetate, butyl acetate, methyl propionate, ethyl propionate, methyl butyrate, propyl butyrate, methyl valerate, dimethyl oxalate, diethyl oxalate, and dimethyl succinate.

Suitable aliphatic ethers used in this invention are those containing 2 to 8 carbon atoms, such as dimethyl ether, diethyl ether, methyl ethyl ether, dipropyl ether, and dibutyl ether.

The reaction can be carried out advantageously by using at least one metal of Group VIII of the periodic table as a main catalyst and at least one iodine-containing substance selected from iodine and iodine compounds as a promotor. The metal of Group VIII of the periodic table are iron, nickel, cobalt, ruthenium, rhodium, palladium, osmium, iridium and platinum, and compounds of these having an optional atomic valence can be used. Examples are iron iodide, iron carbonyl, cobalt iodide, cobalt carbonyl, nickel iodide, nickel carbonyl, nickel acetate, nickel powder, nickel acetyl acetonate, $RhCl_3$, $[RhI(CO)_2]_2$, $RhBr(P\phi_3)_3$, $Rh(CO)_3$, $[Rh(CH_3COO)_2]_2$, $IrCl_3$, $Ir_2(CO)_4I_2$, $Ir_2(CO)_8$, $Ir(SnCl_3)(P\phi_3)_3$, $IrI(CO)(Sb\phi_3)_2$, $PdI_2$, $[Pd(P\phi_3)_2]Cl_2$, $Pd[(n-C_4H_9)_3P](CO)Cl_2$, $RuBr_3$, $Ru(CO)_{12}$, $RuI_2(CO)$-

(Asφ₃)₃, H₂PtCl₆, Pt(Asφ₃)₂, Os(CO)₅, and OsBr₃(Asφ₃)₂. φ in the above exemplification represents a phenyl group.

As a promotor, iodine and various compounds containing an iodine atom can be utilized. Examples of especially suitable promoters are as follows:

$$RI_n \quad (II)$$

wherein R represents hydrogen or alkyl, and n is 1 to 3, $$I_2 \text{ or } I_3^- \quad (III)$$

$$RCOI \quad (IV)$$

wherein R is alkyl, $$MI_n \quad (V)$$

wherein M is an alkali or alkaline earth metal, and n is 1 or 2, $$R_4MI, R_4MI_3, \text{ or } R_3MI_2 \quad (VI)$$

wherein R is hydrogen, alkyl or aryl, and M is a nitrogen, phosphorus, arsenic or antimony atom.

Examples of suitable iodine-containing compounds as promoters are $I_2$, $KI_3$, HI, $CH_3I$, $C_2H_5I$, $C_3H_7I$, $C_4H_9I$, $CH_2I_2$, $C_2H_4I_2$, $CHI_3$, $CH_3COI$, $C_2H_5COI$, NaI, KI, LiI and $CaI_2$.

In the present invention, the reaction can be performed by using a combination of the main catalyst and the promoter exemplified hereinabove. To quicken the rate of the reaction, an organic accelerating agent can be added. Suitable organic accelerating agents are compounds capable of forming coordination compounds with metals of Group VIII of the periodic table to form a coordination bond in the molecular structure. A wide range of organic compounds of trivalent nitrogen, phosphorus, arsenic or antimony can be used.

Examples of useful organic nitrogen compounds include organic nitrogen compounds of the formula

wherein R₁, R₂ and R₃ are the same or different and represent hydrogen, alkyl or aryl, such as trimethylamine, diethylamine, methyldiethylamine, tributylamine, aniline and dimethylaniline; organic nitrogen compounds of the formula

wherein R₁, R₂ and R₃ are the same or different and each represent hydrogen, alkyl or aryl, such as dimethyl acetamide and N-methyl-N-phenyl acetamide; heterocyclic nitrogen compounds such as pyridine, hydroxyquinoline and imidazole; nitriles such as acetonitrile, propionitrile, adiponitrile and benzonitrile; and ammonium salts such as ammonium acetate.

Examples of compounds of phosphorus, arsenic or antimony are compounds resulting from replacing N of the compounds of formula (VII) by P, As or Sb, such as trimethylphosphine, tributylphosphine, diphenylphosphine, triphenylphosphine, methyldiphenylphosphine, triphenylarsine and triphenylstibine.

The amount of the group VIII metal used as a main catalyst in this invention is generally $10^{-6}$ to 1 mole, preferably $10^{-4}$ to $10^{-1}$ mole, per liter of the starting materials and solvent combined. The amount of the iodine-containing substance used as a promotor is generally $10^{-6}$ to 20 moles, preferably $10^{-4}$ to 10 moles, as iodine atom per liter of the starting materials and solvent combined. The amount of the nitrogen-group element compound required to form a stoichiometric coordination compound with the group VIII metal is generally $10^{-6}$ to 10 moles, preferably $10^{-4}$ to 5 moles, per liter of the starting materials and solvent combined.

The proportion of the phenol used in this invention with regard to the aliphatic carboxylic acid ester or aliphatic ether can be varied over a wide range. Generally, it is 0.001 to 1000 moles, preferably 0.01 to 100 moles, more preferably 0.1 to 10 moles, calculated as phenoxy groups per mole of the carboxyl or alkoxy group. Preferably, the process of this invention is carried out at a temperature of 50° to 300° C., especially 100° to 240° C., and a pressure (as the partial pressure of carbon monoxide) of 0 to 1000 kg/cm², especially 2 to 200 kg/cm².G. Carbon monoxide used needs not to be of high purity, and may contain hydrogen, carbon dioxide, methane, nitrogen, rare gases, water, etc. Carbon monoxide of extremely low purity is not preferred because it will increase the pressure of the reaction system.

A solvent is not particularly required in the process of this invention because the starting aliphatic carboxylic acid ester or aliphatic ether and phenol, and the resulting carboxylic acid and carboxylic acid ester of the phenol act as a solvent. If desired, a solvent may be used in addition to these. Examples of such solvents are organic acids such as acetic acid, propionic acid, butyric acid, octanoic acid, cyclohexylcarboxylic acid, phthalic acid and benzoic acid, ketones such as acetone, methyl ethyl ketone, dibutyl ketone, methyl isobutyl ketone, acetophenone and benzophenone, hydrocarbons such as dodecane, hexadecane, benzene, naphthalene and biphenyl, and inorganic esters such as triphenyl phosphate, tricresyl phosphate, dibutylphenyl phosphate, tetramethyl orthosilicate, and tetrabutyl silicate. The carboxylic acid ester of phenol which is the reaction product in the process of this invention is an especially preferred solvent. Examples of this ester are compounds of the formula

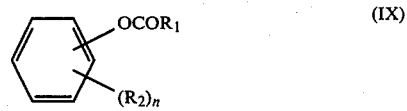

wherein n is an integer of 1 to 5, R₁ represents hydrogen or C₁–C₄ alkyl or alkenyl, and R₂ represents hydrogen, alkyl, aryl, alkenyl, hydroxymethyl, acyl, acyloxy, formyl, carboxy, hydroxy, halogen, sulfo, nitro, nitroso, amino, acid amide, or cyano, and two or more R₂ groups may be the same or different, and the substituents R may be bonded to each other to form a penta- or hexa-carbocyclic or heterocyclic ring. Specifically, they include, for example, phenyl formate, phenyl acetate, phenyl propionate, phenyl butyrate, phenyl valerate, tolyl acetate, xylyl acetate, mesityl acetate, cumenyl acetate, ethylphenyl acetate, propylphenyl acetate, butylphenyl acetate, chlorophenyl acetate, nitrophenyl acetate, nitrosophenyl acetate, aminophenyl acetate, cyanophenyl acetate,

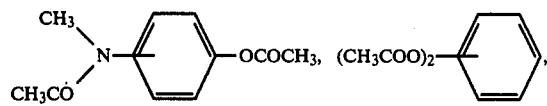

naphthyl acetate, naphthyl propionate, naphthyl butyrate, diacetoxynaphthalene, (diacetoxy)ethyl anthracene, (diacetoxy)aminoanthracene, and diacetoxyanthracene.

The solvent has an effect of maintaining the reaction system substantially anhydrous. In other words, even when a small amount of water is present in the reaction system, the solvent reacts with water by hydrolysis, for example, and serves to remove water within the reaction system.

When, for example, methyl acetate or dimethyl ether and phenol are introduced continuously into a reactor together with the catalyst, they react with separately fed carbon monoxide as follows:

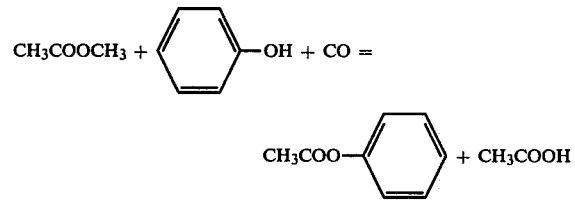

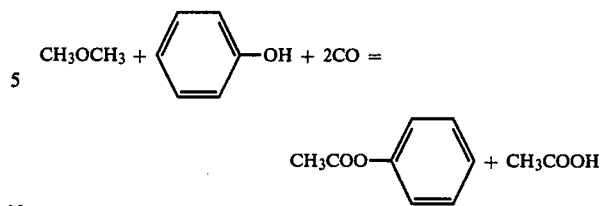

The acetic acid formed can be separated easily from the main reaction product by distillation. Since water is absent in the reaction system, substantially anhydrous acetic acid can be obtained. Phenyl acetate formed simultaneously can be converted to phenol and methyl acetate by reaction with methanol, and therefore has the advantage that it can be recycled together with the catalyst for reuse as the starting material.

The following Examples illustrate the invention more specifically.

EXAMPLES 1 TO 18

The starting materials, main catalysts, promotors, and optionally organic accelerating agents and solvents shown in Table 1 were charged in the indicated amounts into a reactor, and the starting materials were reacted with carbon monoxide (or a gaseous mixture of carbon monoxide and hydrogen) under the reaction conditions indicated in Table 2. The reaction mixture obtained by the reaction was analyzed, and the yield of the product (based on the carboxylic acid ester) was determined. The results are shown in Table 2. Water and hydrogen iodide did not substantially form. The half period denotes the time required for 50% of the starting carboxylic acid ester to be converted to the carboxylic acid.

TABLE 1

| Example | Starting materials Carboxylate (g) | Phenol (g) | Solvent (g) | Catalyst Main catalyst (g) | Promotor (g) | Organic accelerator (g) |
|---|---|---|---|---|---|---|
| 1 | Methyl acetate (67.9) | Phenol (104) | Acetic acid (27.5) | Rhodium chloride (0.105) | Methyl iodide (28.4) | — |
| 2 | Methyl acetate (37) | Phenol (56) | Acetic acid (18) | Rhodium iodide (1.21) | Methyl iodide (14.2) | — |
| 3 | Methyl acetate (37) | Phenol (56.4) | Acetic acid (48) | Rhodium chloride (0.24) | Calcium iodide (29.4) | P$\phi_3$ (1.2) |
| 4 | Methyl acetate (37) | Phenol (56.4) | — | RhCL(CO)(P$\phi_3$)$_2$ (1.0) | Methyl iodide (14.2) | — |
| 5 | Ethyl propionate (51) | Phenol (94) | Propionic acid (18.5) | Rhodium chloride (0.327) | Ethyl iodide (25) | P(n-C$_4$H$_9$)$_3$ (1.2) |
| 6 | Methyl acetate (37) | Phenol (56.4) | Acetic acid (30) | Iridium chloride (0.5) | Methyl iodide (17) | — |
| 7 | Methyl acetate (59.2) | p-Cresol (104) | — | Palladium chloride (1.8) | Methyl iodide (31.5) | P$\phi_3$ (5.8) |
| 8 | Propyl butyrate (65) | Phenol (56.4) | Butyric acid (70.4) | Chloroplatinic acid (0.5) | Calcium iodide (29.4) | P$\phi_3$ (1.0) |
| 9 | Methyl acetate (37) | Phenol (56.4) | Acetic acid (16.5) | Ruthenium chloride (0.5) | Methyl iodide (20) | P$\phi_3$ (1.2) |
| 10 | Ethyl propionate (51) | Phenol (56.4) | Propionic acid (59.2) | Osmium chloride (0.5) | Calcium iodide (29.4) | P$\phi_3$ (1.8) |
| 11 | Methyl acetate | Phenol | — | Cobalt bromide | Methyl iodide | P$\phi_3$ |

TABLE 1-continued

| Ex- ample | Starting materials | | | Catalyst | | |
|---|---|---|---|---|---|---|
| | Carboxylate (g) | Phenol (g) | Solvent (g) | Main catalyst (g) | Promotor (g) | Organic accelerator (g) |
| 12 | Methyl acetate (62) | Phenol (78.8) | — | Nickel acetyl acetate (2.5) | Methyl iodide (31.5) | P$\phi_3$ (12) |
| 13 | Methyl acetate (62) | Phenol (78.8) | — | Iron carbonyl (2.57) | Methyl iodide (35.5) | Triethyl- amine (58) |
| 14 | Methyl acetate (62) | Hydro- quinone (66) | Acetic acid (60) | RhCl(CO)(P$\phi_3$)$_2$ (0.8) | Methyl iodide (35.5) | (1.7) |
| 15 | Propyl butyrate (74) | p-Chloro- phenol (77) | Benzene (100) | RhCl(CO)(P$\phi_3$)$_2$ (1.0) | Methyl iodide (14.2) | — |
| 16 | Diethyl ether (65) | Phenol (56.4) | Propionic acid (59.2) | RhCl(CO)(P$\phi_3$)$_2$ (1.0) | Calcium iodide (29.4) | — |
| 17 | Dimethyl succinate (37) | Dihydroxy- naphthalene (112) | Acetic acid (120) | RhCl(CO)(P$\phi_3$)$_2$ (1.0) | Calcium iodide (29.4) | — |
| 18 | Dimethyl ether (43.8) (23) | Phenol (56.4) | Acetic acid (30) | RhCl(CO)(P$\phi_3$)$_2$ (1.0) | Methyl iodide (14.2) | — |

TABLE 2

| Ex- ample | Reaction conditions | | | Half period (minutes) | Yield of the product including the solvent (g/%) | |
|---|---|---|---|---|---|---|
| | Tempera- ture (°C.) | Total pressure (kg/cm² · G) | Partial pressure of CO (kg/cm² · G) | | | |
| 1 | 180 | 35 | 30 | 300 | Acetic acid (81.2/97.5) | Phenyl acetate (120.8/96.8) |
| 2 | 180 | 25 | 20 | 165 | Acetic acid (47/96.7) | Phenyl acetate (66.5/97.8) |
| 3 | 180 | 36 | 30 | 39 | Acetic acid (77.3/97.7) | Phenyl acetate (65.6/96.5) |
| 4 | 190 | 38 | 30 | 84 | Acetic acid (29.0/96.7) | Phenyl acetate (66.8/98.2) |
| 5 | 180 | 34 | 30 | 250 | Propionic acid (53.0/93.2) | Phenyl propionate (70.4/93.9) |
| 6 | 180 | 37 | 30 | 320 | Acetic acid (57.6/92.0) | Phenyl acetate (62.4/91.8) |
| 7 | 195 | 38 | 28 | 480 | Acetic acid (46.0/95.8) | p-Tolyl acetate (114.7/95.6) |
| 8 | 180 | 157 | 150 | | Butyric acid (75.2/10.9) | Phenyl butyrate (8.1/11.1) |
| 9 | 180 | 47 | 40 | 280 | Acetic acid (43.1/88.7) | Phenyl acetate (60.2/88.5) |
| 10 | 180 | 157 | 150 | | Propionic acid (62.6/9.2) | Phenyl propionate (8.3/11.1) |
| 11 | 190 | 190 | 180 | | Acetic acid (37.7/75.0) | Phenyl acetate (84.3/74.0) |
| 12 | 180 | 48 | 30 (10*) | 120 | Acetic acid (48.5/96.4) | Phenyl acetate (111.5/97.8) |
| 13 | 195 | 160 | 150 | | Acetic acid (35.91/71.4) | Phenyl acetate (82.7/72.5) |
| 14 | 200 | 40 | 30 | 28 | Acetic acid (119.2/98.7) | Hydroquinone monoacetate (33.7/22.2) Hydroquinone diacetate (73.3/75.6) |

*The partial pressure of hydrogen

| Ex- ample | Reaction conditions | | | Half period (minutes) | Yield of the product including the solvent (g/%) | |
|---|---|---|---|---|---|---|
| | Tempera- ture (°C.) | Total pressure (kg/cm² · G) | Partial pressure (kg/cm² · G) | | | |
| 15 | 200 | 40 | 30 | | Butyric acid (33.1/75.2) | p-Chlorophenyl butyrate (73.5/75.0) |
| 16 | 180 | 40 | 30 | | Propionic acid (93.4/92.4) | Phenylpropionate (69.1/92.1) |
| 17 | 190 | 34 | 30 | | Succinic acid (26.6/75.1) | Dihydroxy- naphthalene |

TABLE 2-continued

| | | | | | |
|---|---|---|---|---|---|
| | | | | | diacetate (90.8/74.9) |
| 18 | 190 | 50 | 30 | Acetic acid (59.2/97.3) | Phenyl acetate (66.1/97.2) |

EXAMPLE 19

37.0 g of methyl acetate, 56.4 g of phenol, 30 g of acetic acid, 0.188 g of rhodium acetate, 18.8 g of methyl iodide and 0.29 g of 2,6-lutidine were placed into a pressure vessel, and it was pressurized by CO gas to a total pressure of 19 kg/cm$^2$.G (CO partial pressure 10 kg/cm$^2$.G) at a temperature of 200° C.

Reaction was carried out at constant pressure and 59.1 of acetic acid and 64.4 g of phenylacetate were obtained in the reaction solution. The theoretical yields based on the methyl acetate as a starting material were 97.0% and 94.7% respectively. The half period was 18 minutes.

This reaction solution was distilled at atmospheric pressure and 17.64 g of the liquor containing mainly methyl iodide and 30.0 g of crude acetic acid (98.5% of purity) was obtained as an initial boiling fraction. The distillation residue, initial boiling fraction and 16 g of methanol were mixed and heated for a fixed time in a sealed tube. The reaction solution contained 36.2 g of methylacetate and 55.1 g of phenol, and methanol was not detected at all.

The resulting reaction solution was pressurized by carbon monoxide gas to a total pressure of 19 kg/cm$^2$.G (the partial pressure of CO 10 kg/cm$^2$.G) at a temperature of 200° C. The reaction was carried out by the same method as above at a fixed pressure and 59.0 g of acetic acid and 63.9 g of phenyl acetate were obtained in the reaction solution. The half period was 20 minutes.

What we claim is:

1. A process for producing an aliphatic carboxylic acid and an aliphatic carboxylic acid ester of an aromatic hydroxy compound which comprises reacting (A) an aromatic hydroxy compound selected from the group consisting of phenol, cresol, xylenol, trimethylphenol, tetramethylphenol, pentamethylphenol, ethylphenol, propylphenol, thymol, 2-methyl-5-isopropylphenol, butylphenol, amylphenol, octylphenol, methyldibutylphenol, diethylphenol, catechol, resorcinol, hydroquinone, dihydroxytoluene, hexylresorcinol, pyrogallol, phloroglucinol, chlorophenol, bromophenol, nitrophenol, nitrosophenol, aminophenol, N,N-dimethylaminophenol, N-methyl-N-acetyl-phenol, acetyloxyphenol, formylphenol, cyanophenol, phenolsulfonic acid, hydroxymethylphenol, naphthol, dihydroxynaphthalene, dihydronaphthol, tetrahydronaphthol, phenylphenol, hydroxyquinolin, anthrahydroquinone, methylanthrahydroquinone, ethylanthrahydroquinone, amylanthrahydroquinone, and 1,2-dihydroxyanthraquinone, (b) (1) an aliphatic carboxylic acid ester formed between an aliphatic carboxylic acid having 1 to 5 carbon atoms and an alcohol having 1 to 4 carbon atoms and selected from the group consisting of methyl formate, propyl formate, methyl acetate, ethyl acetate, butyl acetate, methyl propionate, ethyl propionate, methyl butyrate, propyl butyrate, methyl valerate, dimethyl oxalate, diethyl oxalate, and dimethyl succinate or (2) an aliphatic ether of 2 to 8 carbon atoms selected from the group consisting of dimethyl ether, diethyl ether, methyl ethyl ether, dipropyl ether, and dibutyl ether, and (C) carbon monoxide at a temperature of from 50°–300° C. and a reaction pressure of 0–1000 kg./cm$^2$ G in the presence of a catalyst composed of at least one metal of Group VIII of the periodic table and a promotor composed of at least one iodine-containing substance selected from the group consisting of iodine and iodine compounds and separating and recoving the thus produced aliphatic carboxylic acid from the reaction mixture.

2. A process according to claim 1 wherein the reaction is carried out in the presence of an organic accelerating agent composed of an organic compound of a trivalent nitrogen-group element.

3. A process according to claim 1 wherein the reaction is carried out in the presence of a solvent.

4. A process according to claim 1 wherein the ester of the aliphatic carboxylic acid with the aromatic hydroxy compound is separated and recovered from the reaction mixture, reacted with the alcohol having 1 to 4 carbon atoms to convert it into the aromatic hydroxy compound and the carboxylic acid ester of the aliphatic alcohol, and the converted products are recycled as starting materials.

* * * * *